(12) United States Patent
Kwon et al.

(10) Patent No.: US 9,060,828 B2
(45) Date of Patent: Jun. 23, 2015

(54) ULTRASONIC TIP FOR AN APICOECTOMY, AND METHOD FOR MANUFACTURING SAME

(75) Inventors: Young Sam Kwon, Gyeongsangnam-do (KR); In Hwan Lee, Gyeonggi-do (KR)

(73) Assignees: CETATECH, INC., GYEONGSANGNAM-DO (KR); B&L BIOTECH CO., LTD., Gyeonggi-Do (KR)

( * ) Notice: Subject to any disclaimer, the term of this patent is extended or adjusted under 35 U.S.C. 154(b) by 0 days.

(21) Appl. No.: 13/581,449

(22) PCT Filed: Aug. 25, 2010

(86) PCT No.: PCT/KR2010/005706
§ 371 (c)(1),
(2), (4) Date: Nov. 1, 2012

(87) PCT Pub. No.: WO2011/105669
PCT Pub. Date: Sep. 1, 2011

(65) Prior Publication Data
US 2013/0040261 A1    Feb. 14, 2013

(30) Foreign Application Priority Data
Feb. 25, 2010    (KR) .................. 10-2010-0016889

(51) Int. Cl.
*B22F 3/24*    (2006.01)
*A61C 3/03*    (2006.01)
*A61B 17/00*   (2006.01)
*A61B 17/32*   (2006.01)

(52) U.S. Cl.
CPC ......... *A61C 3/03* (2013.01); *A61B 2017/00526* (2013.01); *A61B 2017/320076* (2013.01)

(58) Field of Classification Search
USPC ............. 419/28, 29, 36, 37; 433/29, 119
See application file for complete search history.

(56) References Cited

U.S. PATENT DOCUMENTS 5,682,665 A * 11/1997 Svanberg ............ 29/458
5,848,350 A * 12/1998 Bulger ................ 419/36
(Continued)

FOREIGN PATENT DOCUMENTS

JP         09-140727 A    6/1997
KR     10-2002-0025067 A    4/2002
(Continued)

OTHER PUBLICATIONS

International Search Report (with English Translation) for International Application No. PCT/KR2010/005706, dated Apr. 25, 2011.
(Continued)

*Primary Examiner* — George Wyszomierski
*Assistant Examiner* — Ngoclan T Mai
(74) *Attorney, Agent, or Firm* — Heslin Rothenberg Farley & Mesiti P.C.

(57) ABSTRACT

The invention relates to a method for manufacturing an ultrasonic tip for an apicoectomy, such that the tip has a shape suitable for the shape of a tooth root, comprising the steps of: forming a feedstock by mixing a metal powder including stainless steel with a binder; injecting the feedstock to form an injection-molded part having a plurality of projections integrally formed on the surface thereof; performing debinding to remove the binder from the injection-molded part; sintering the injection-molded part; and performing annealing to increase the ductility and facilitate the bending of the sintered part.

15 Claims, 8 Drawing Sheets

(56) References Cited

U.S. PATENT DOCUMENTS

| | | | |
|---|---|---|---|
| 6,422,865 B1 * | 7/2002 | Fischer | 433/81 |
| 7,875,237 B2 * | 1/2011 | Hwang et al. | 419/66 |
| 2004/0023187 A1 * | 2/2004 | Hickok | 433/119 |
| 2005/0181328 A1 * | 8/2005 | Milne | 433/119 |
| 2006/0185170 A1 * | 8/2006 | Lewis et al. | 29/896.11 |
| 2008/0254409 A1 | 10/2008 | Hwang et al. | |
| 2009/0081603 A1 | 3/2009 | Forster | |

FOREIGN PATENT DOCUMENTS

| | | |
|---|---|---|
| KR | 10-0901328 B1 | 6/2009 |
| KR | 10-0912272 B1 | 8/2009 |
| KR | 10-0935472 B1 | 1/2010 |

OTHER PUBLICATIONS

Extended search report issued by the European Patent Office on Jul. 24, 2013 for corresponding EP Patent Application No. 10846696.2.

* cited by examiner

100

ULTRASONIC TIP FOR AN APICOECTOMY, AND METHOD FOR MANUFACTURING SAME

CROSS REFERENCE TO RELATED APPLICATIONS

This application is a national stage filing under section 371 of International Application No. PCT/KR2010/005706, filed on Aug. 25, 2010, and published in Korean on Sep. 1, 2011, as WO 2011/105669 and claims priority to Korean Application No. 10-2010-0016889 filed on Feb. 25, 2010. The entire disclosures of each of these applications are incorporated herein by reference.

TECHNICAL FIELD

The present invention relates to an ultrasonic tip for an apicoectomy of a dental clinic, and more particularly, to an ultrasonic tip for an apicoectomy and a method for manufacturing the ultrasonic tip that may correspond to anatomical diversity of a tooth root and may enhance a lifespan and a durability

BACKGROUND ART

A surgical apicoectomy is the most common procedure for a surgical root treatment. Due to development of equipment and instruments, extracted teeth are preserved in an oral cavity. Recently, an importance of the surgical root treatment is further being extended and generalized.

A most salient technology of the surgical apicoectomy is performed to remove an infected nerve tissue in a tooth root and to form a cavity, in order to perform retrograde filling along a root canal in the tooth root in a root apex after incising the root apex. In this instance, the nerve tissue is typically removed using an ultrasonic tip. Using of the ultrasonic tip may minimize an incision during a surgery, and may minimize damage to a soft tissue, compared to a handpiece, and accordingly post-surgery side effects may be minimized and a quick wound healing may be expected.

However, since a conventional ultrasonic tip is manufactured by mechanical processing, it may be difficult to improve a processing precision, and only a material suitable for the mechanical processing may be used for the conventional ultrasonic tip. In addition, manufacturing costs may increase and a processing speed may decrease, which may act as disadvantages for a mass production.

Additionally, to delete a nerve tissue, a diamond coating layer is formed on a surface of the conventional ultrasonic tip. However, since diamond particles are easily dropped from the coating layer, a durability and a lifespan may be reduced, and a precision and convenience of a treatment may be deteriorated. In addition, when a leading edge of the conventional ultrasonic tip is modified a little, a diamond coating layer of the leading edge may be damaged, and accordingly the leading edge may not function normally.

Since teeth have various anatomical structures for each tooth, rather than having standardized anatomical structures, there is a need to develop an ultrasonic tip having different angles and different lengths based on a shape of each tooth. Conventional ultrasonic tips having various shapes are being sold, however, angles and lengths of conventional ultrasonic tips are fixed, and accordingly conventional ultrasonic tips may not be matched to various anatomical structures of teeth. Accordingly, it is difficult to perform surging using conventional ultrasonic tips, and an unnecessary dentine may be removed. Additionally, since a larger number of root apexes need to be incised, a long period of time may be required for a surgery, and post-surgery side effects and a recovery time may be increased.

DISCLOSURE OF INVENTION

Technical Goals

An aspect of the present invention provides an ultrasonic tip for an apicoectomy and a method for manufacturing the ultrasonic tip that may simplify a manufacturing process of the ultrasonic tip and that may reduce manufacturing costs.

Additionally, another aspect of the present invention provides an ultrasonic tip for an apicoectomy and a method for manufacturing the ultrasonic tip that may correspond to various anatomical shapes of a tooth root.

Furthermore, another aspect of the present invention provides an ultrasonic tip for an apicoectomy and a method for manufacturing the ultrasonic tip that may enhance a durability and a reliability and that may extend a lifespan.

Moreover, another aspect of the present invention provides an ultrasonic tip for an apicoectomy and a method for manufacturing the ultrasonic tip that may improve a treatment efficiency and that may improve a precision and a convenience of a treatment.

Technical Solutions

According to an aspect of the present invention, there is provided a method for manufacturing an ultrasonic tip for an apicoectomy, including: forming a feedstock by mixing a metal powder including stainless steel with a binder; injecting the feedstock to form an injection-molded part having a plurality of projections integrally formed on the surface thereof; performing debinding to remove the binder from the injection-molded part; sintering the injection-molded part; and performing annealing to increase a ductility and facilitate a bending of the sintered part.

In this instance, the ultrasonic tip may include a shank portion, a body portion, and a leading edge portion, and the annealing may be performed so that the body portion and the leading edge portion may be bendable. Additionally, the annealing may be performed at a temperature of 400° C. to 1250° C.

Additionally, the method may further include bending a part of the leading edge portion to form the leading edge portion to be suitable for a shape and an angle of a tooth root. The bending may be performed after manufacturing the ultrasonic tip, namely, after the annealing, or may be performed by a practitioner prior to a procedure.

Each of the projections may be formed in one or at least two selected from among a circular conic shape, a polygonal pyramid shape, a truncated conic shape, a truncated polygonal pyramid shape, a circular cylindrical shape, a polyhedral shape, and an ellipsoidal shape. Additionally, the projections may have the same size and the same shape, or may have different sizes and different shapes.

According to an aspect of the present invention, there is provided an ultrasonic tip for an apicoectomy, including: a shank portion connected to a driving portion (not shown) to provide driving power; a body portion extending from the shank portion; and a leading edge portion extending integrally from an end of the body portion and including a plurality of projections integrally formed on a surface thereof. The shank portion, the body portion, and the leading edge portion may be integrally formed using powder injection molding (PIM), and the body portion and the leading edge portion may have a ductility to be bendable.

In this instance, the shank portion, the body portion, the leading edge portion, and the projections may be formed by PIM, using a metal powder including stainless steel.

Additionally, each of the projections may be formed in one or at least two selected from among a circular conic shape, a polygonal pyramid shape, a truncated conic shape, a truncated polygonal pyramid shape, a circular cylindrical shape, a polyhedral shape, and an ellipsoidal shape. The projections may have the same size and the same shape, or may have different sizes and different shapes. In addition, the projections may be arranged linearly along a length of the leading edge portion, or may be arranged spirally along a circumference of the leading edge portion. The leading edge portion may have a cross-sectional area that tapers towards an end of the leading edge portion, and the projections may become smaller towards the end.

Effect of Invention

As described above, according to embodiments of the present invention, it is possible to manufacture an ultrasonic tip for an apicoectomy including tip projections that are integrally formed, using powder injection molding (PIM).

Additionally, according to embodiments of the present invention, PIM may facilitate manufacturing of an ultrasonic tip and may reduce costs and time, by simplifying a manufacturing process of the ultrasonic tip. In addition, due to good productivity, the ultrasonic tip may be advantageous for a mass production.

Furthermore, according to embodiments of the present invention, since fine projections are integrally formed on a surface of an ultrasonic tip and are densely arranged, it is possible to enhance a precision, compared to mechanical processing, and to improve a precision and a convenience of a treatment.

Moreover, according to embodiments of the present invention, a practitioner may flexibly respond to various shapes of a tooth root by properly modifying an ultrasonic tip, and accordingly a procedure may be quickly performed based on an anatomical structure of a root apex. Thus, it is possible to reduce a surgery time, and to prevent an unnecessary dentin from being removed.

In addition, according to embodiments of the present invention, since projections are formed integrally with an ultrasonic tip, it is possible to prevent the projections from being eliminated, and to enhance a durability and reliability of the ultrasonic tip.

BEST MODE FOR CARRYING OUT THE INVENTION

Figure 1:
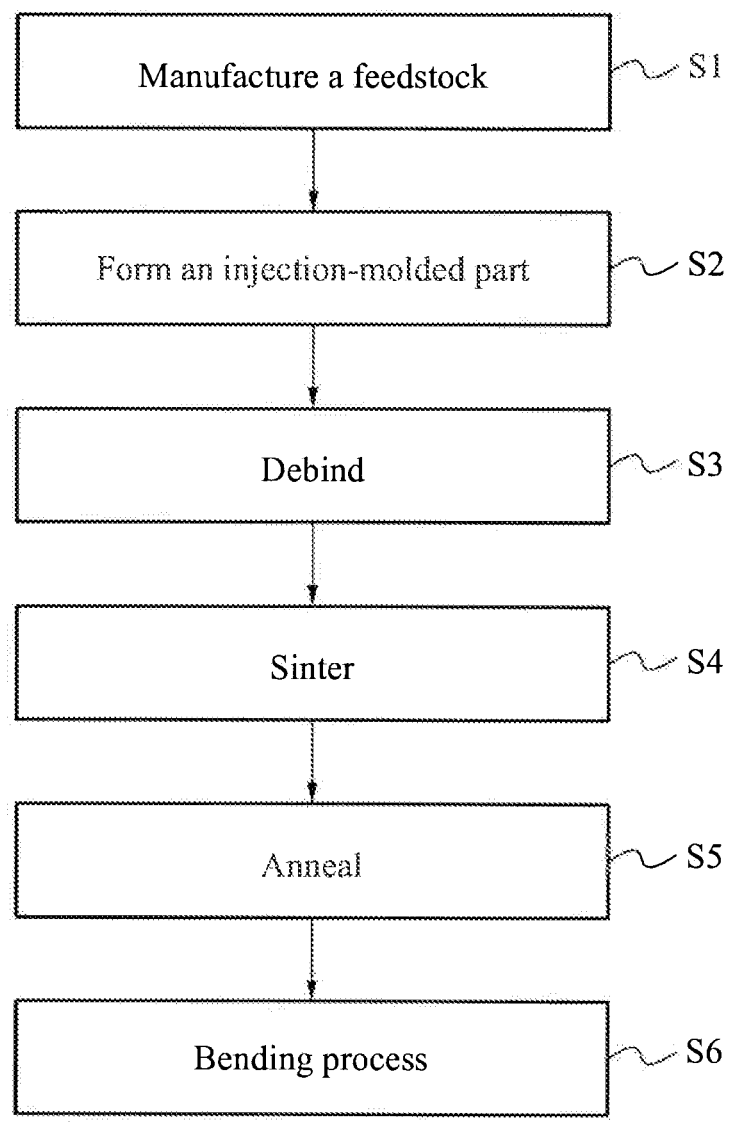
FIG. 1 is a flowchart illustrating a method of manufacturing an ultrasonic tip for an apicoectomy according to an embodiment of the present invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 2:
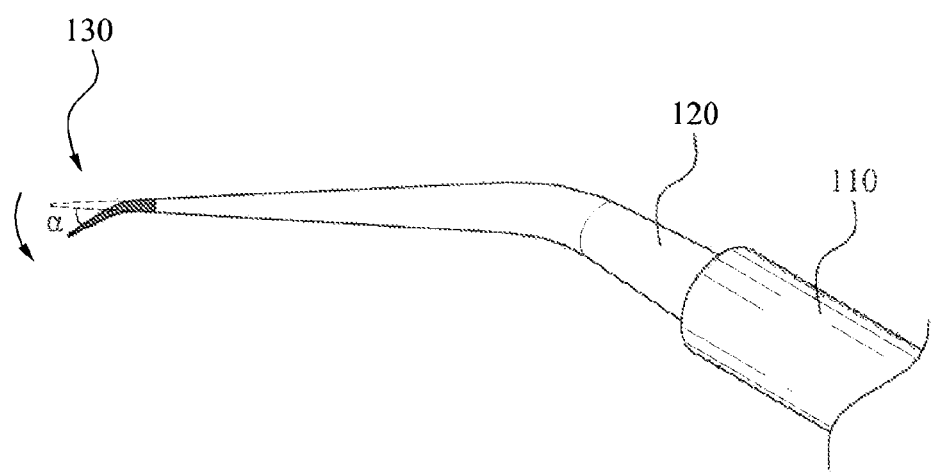
FIG. 2 is a perspective view illustrating an ultrasonic tip for an apicoectomy manufactured by the method of FIG. 1.

Hereinafter, an ultrasonic tip for an apicoectomy, and a method for manufacturing the ultrasonic tip according to an embodiment of the present invention will be described in detail with reference to FIGS. 1 through 8. FIG. 1 is a flowchart illustrating a method of manufacturing an ultrasonic tip for an apicoectomy according to an embodiment of the present invention, and FIG. 2 is a perspective view illustrating an ultrasonic tip for an apicoectomy according to an embodiment of the present invention. FIGS. 3 through 8 are perspective views illustrating examples of projections of an ultrasonic tip according to embodiments of the present invention.

As illustrated in the drawings, an ultrasonic tip 100 for a surgical apicoectomy may refer to an apparatus for removing a dentin and forming a cavity while rotating in a low speed or a high speed, to incise a root apex. The ultrasonic tip 100 may broadly include a shank portion 110 and a body portion 120 that are connected to an apparatus (not shown) to provide rotatory power, and a leading edge portion 130 used to remove a dentin. Additionally, the leading edge portion 130 may include a plurality of projections 131 to 138 of FIGS. 3 through 8 that are integrally formed with the leading edge portion 130 and that are substantially in contact with a target dentin to remove the target dentin. In particular, the ultrasonic tip 100 may be formed using powder injection molding (PIM).

The ultrasonic tip 100 is described as an example in the present embodiment, however, the present invention is not limited to embodiments. The ultrasonic tip 100 may be applied to an apparatus for removing tartar attached onto teeth or other foreign substances attached onto the teeth, as well as, to various apparatuses for dental treatments, such as various endodontic treatments by rotation or oscillation (for example, a root canal surgery), an implant surgery, a periodontal surgery, an oral surgery, a maxillofacial surgery, and the like. In addition to the dental treatments, the ultrasonic tip 100 may be applied to an apparatus for procedures, such as osteotomy and drilling that are orthopedic procedures of bones, saucerization of thinly removing a cortical bone, and the like, and for procedures, such as an oscillation by a mechanical saw blade that is a beauty-oriented procedure, rasp of a bone using a reciprocation and a polishing tool, and the like.

Referring to FIG. 1, the ultrasonic tip 100 may be manufactured through operation S11 of forming a feedstock including power, operation S12 of injecting the feedstock to form an injection-molded part, operation S13 of performing debining on the injection-molded part, and operation S14 of performing sintering. Additionally, operation S15 of performing annealing to increase a ductility so that a practitioner may freely modify the ultrasonic tip 100, and operation S16 of performing bending may be performed.

Specifically, to form the ultrasonic tip 100, the feedstock may be formed by mixing a predetermined powder with a binder in operation S11.

The feedstock may refer to a fluid having a predetermined viscosity to enable the powder to be supplied to a mold for general injection molding, and may be formed by mixing the binder with powder, namely a material used to form the ultrasonic tip 100, in a predetermined ratio at an appropriate temperature. In this instance, a mixing ratio of the powder and the binder in the feedstock may variously vary depending on requirements.

Injection molding may be performed using metal powder or stainless steel powder to have a predetermined strength so that the ultrasonic tip 100 may remove the dentin. Alternatively, as the powder, ceramic powder, such as zirconia or alumina, metal powder, such as tungsten carbide or stainless steel, or a mixture of the ceramic powder and metal powder may be used. Additionally, a mixture of metal powder, non-metal powder, and ceramic powder may be used, as well as a single type of powder. The binder may provide a fluidity enabling the feedstock to be uniformly injected into a mold during an injection process, and may be used to enhance strength of an injection-molded part. In this instance, a typical single binder may be used, and various types of binders having different melting points may be used together according to circumstances. For example, a paraffin wax, polyethylene, polypropylene, stearic acid, and the like may be mixed with each other to from the binder. Additionally, the binder may include a binding material, a lubricant, a plasticizer, a surfactant, and the like.

Subsequently, the feedstock may be injected into a mold having a shape of the ultrasonic tip 100, and the injection-molded part may be formed in operation S12.

The injection-molded part may be extracted by injecting the feedstock into a mold having a predetermined shape, and by cooling/solidifying the feedstock, so that the shank portion 110, the body portion 120, and the leading edge portion 130 that has the projections may be integrally formed. In this instance, the injection-molded part may be formed to have a volume greater than a size of the final ultrasonic tip 100, based on a reduction in the volume during operations S13 and S14 that will be described later.

Subsequently, the debinding may be performed to remove, from the injection-molded part, the binder added during manufacturing of the feedstock in operation S13.

When the feedstock includes a plurality of binders having different characteristics (for example, a melting point), operation S13 may be substantially performed several times, instead of once. For example, in operation S13, solvent debinding may be performed using a solvent, such as N-hexane, heptane, thinner, and the like, to remove waxes, such as paraffin wax and the like, from the binder, and thermal debinding may be performed by applying heat to the solvent debound injection-molded part, to remove the binder. Additionally, other debinding processes, for example, electrolytic degreasing, ultrasonic degreasing, and the like may be applicable, in addition to the solvent debinding and the thermal debinding.

Subsequently, the debound injection-molded part may be sintered at a predetermined temperature in operation S14.

In operation S14, a sintering temperature, a sintering time, and a sintering atmosphere may be determined based on a particle size and a type of powder used in the feedstock, and a type of additives. Additionally, when the thermal debinding is performed on the injection-molded part, the sintering and the thermal debinding may be performed simultaneously. In other words, the solvent debound injection-molded part may be inserted in a sintering furnace, and may be heated at a predetermined temperature, so that the thermal debinding and the sintering may be performed simultaneously. Thus, it is possible to improve productivity by reducing a process.

Subsequently, the sintered part may be annealed at a predetermined temperature in operation S15, so that the ultrasonic tip 100 having a predetermined ductility may be formed. Additionally, the annealed ultrasonic tip 100 may be bent by a predetermined length and at a predetermined angle in operation S16, so that the ultrasonic tip 100 may have a shape suitable for a shape of a tooth root.

As shown in FIG. 2, the ultrasonic tip 100 may include the shank portion 110, the body portion 120, and the leading edge portion 130 that are integrally formed by PIM. For example, the shank portion 110 may connected to an external device, and there is no limitation to a shape of the drawing. The body portion 120 may extend from the shank portion 110, and may have a shape of a bar or rod approximately having a circular section. For convenience of a procedure, the body portion 120 may be bent by a predetermined length and at a predetermined angle. Additionally, the leading edge portion 130 may extend from the body portion 120, and may have a cross-sectional area that tapers towards an end thereof. On the surface of the leading edge portion 130, a plurality of fine projections each having a predetermined size and a predetermined height may be densely formed. The projections are not shown in FIG. 2, and will be further described later with reference to FIGS. 3 through 8.

In the ultrasonic tip 100, the body portion 120 and the leading edge portion 130 may be freely bent at a predetermined angle, by a predetermined length. In this instance, a bending length and angle of the ultrasonic tip 100 may substantially, variously vary depending on a shape of a tooth root on which a procedure is to be performed.

In this instance, the present invention is not limited to the drawings, and the shape of the ultrasonic tip 100 may be substantially, variously changed. For example, the body portion 120 and the leading edge portion 130 may have a polygonal cross section, or may be divided into a plurality of surfaces since a plurality of taper surfaces formed on a surface thereof.

Additionally, teeth may have various shapes based on teeth and patients, instead of having a standardized anatomical structure. For convenience of a medical treatment and minimization of a size of an incised part, the ultrasonic tip 100 may need to have an appropriate length and angle based on a shape of a tooth root of each tooth. However, it is realistically difficult to manufacture an ultrasonic tip individually for each case, due to costs, time, and the like.

In the present embodiment, the ultrasonic tip 100 may be formed to have ductility, and accordingly a practitioner may freely change the length and angle of the ultrasonic tip 100 based on a direction and length of a tooth root during a procedure, so that it may have a shape corresponding to an angle and length corresponding to a root canal formed in a major axis of a tooth. Additionally, since the shape of the ultrasonic tip 100 is modified to a shape suitable for a tooth root, as described, a size of an incised part including a bone may be minimized during the procedure, removal of an unnecessary dentin may be prevented, bleeding may be reduced, post-surgery side effects may be minimized, and fast healing may be expected.

In this instance, the shape of the ultrasonic tip 100 may be modified by bending the leading edge portion 130 of the ultrasonic tip 100 at a predetermined angle and by a predetermined length after performing annealing in manufacturing of the ultrasonic tip 100. Alternatively, the ultrasonic tip 100 having the ductility and a predetermined shape may be manufactured, and a practitioner may properly modify the shape of the ultrasonic tip 100 during a procedure. Alternatively, the length and angle of the ultrasonic tip 100 may be approximately bent in manufacturing of the ultrasonic tip 100, and a practitioner may minutely modify and adjust the length and angle of the ultrasonic tip 100 to be suitable for the shape of the tooth root during a procedure.

Additionally, since the leading edge portion 130 and the projections are integrally formed by PIM in the ultrasonic tip 100, the projections may be prevented from being separated and eliminated while the ultrasonic tip 100 is operated, and accordingly durability and reliability may be increased. Furthermore, it is realistically difficult to uniformly process protrusions of tens of micron through general mechanical processing, whereas uniform and fine protrusions may be formed using a PIM technology. In this instance, in an operation of extracting, debinding and sintering an injection-molded part, the injection-molded part may be partially shrunk. Since the projections are formed integrally with the injection-molded part, the injection-molded part may be shrunk, and the projection may also be shrunk, and accordingly fine protrusions may be formed. Additionally, since the injection-molded part may be shrunk at an identical ratio in directions X, Y, and Z, a uniform density of the projection may be maintained, and the size and density of the projection may be uniformly maintained with respect to an entire surface of the leading edge portion 130.

Additionally, the ultrasonic tip 100 may be manufactured using PIM, and accordingly there is an advantage in that conditions, such as shapes, sizes, arrangement of projections and the like may be variously changed based on a design specification, during formation of a mold and an injection-molded part.

For example, a projection may be formed in a contactable shape, using one of a point contact, a line contact, and a surface contact with a target. Additionally, a projection may be provided in one of a circular conic shape or a polygonal pyramid shape (for example, a quadrangular pyramid, a trigonal pyramid, and the like), a frustum of the circular conic shape and the polygonal pyramid shape (for example, a truncated conic shape, a truncated polygonal pyramid shape, and the like), a circular cylindrical shape, a polyhedral shape (for example, a pentahedral shape, a hexahedral shape, and the like), and an ellipsoidal shape.

Hereinafter, various examples of projections of the ultrasonic tip 100 will be described with reference to FIGS. 3 through 8. For reference, embodiments shown in FIGS. 3 through 8 are substantially the same, except shapes of projections, and accordingly like reference numerals are assigned to the same or equivalent elements and thus further descriptions related thereto will be omitted here for convenience of description.

Figure 3:
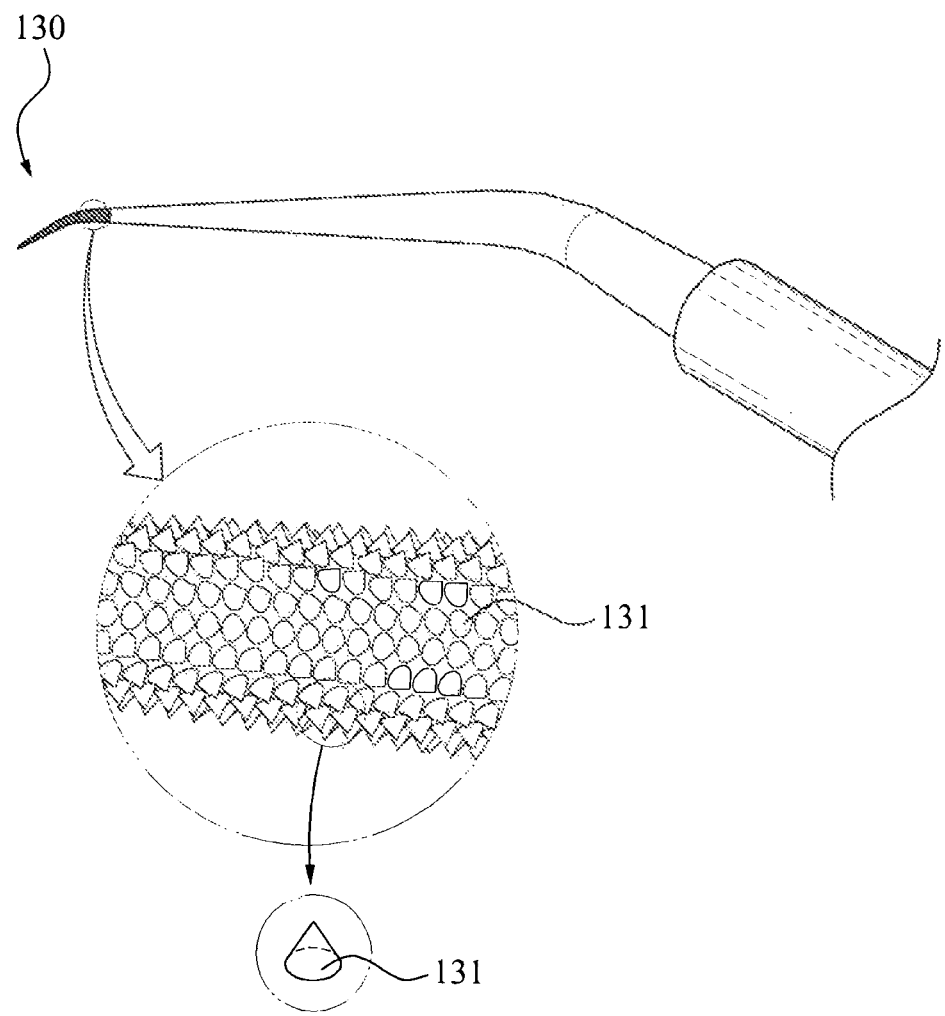
FIGS. 3 through 8 are perspective views illustrating examples of projections of an ultrasonic tip according to embodiments of the present invention.

Referring to FIG. 3, in the ultrasonic tip 100, the shank portion 110, the body portion 120, and the leading edge portion 130 in which a plurality of projections 131 are densely formed, may be integrally formed by PIM.

According to an embodiment of the present invention, each of the projections 131 may be protruded from the surface of the leading edge portion 130 by a predetermined height, and may have a circular conic shape to enable a point contact with a target. Specifically, each of the projections 131 may be formed in a circular conic shape having a sharp vertex and a circular base side (hereinafter, a side of each of the projections 131 in contact with the surface of the leading edge portion 130 is referred to as a 'base side'). Additionally, each of the projections 131 may have a shape of a vertical circular cone in which an axis is perpendicular to the base side, or an axis of each of the projections 131 may be inclined at a predetermined angle with respect to the base side according to circumstances. However, the shape of the projections 131 is not limited by the drawings, and inclination, a height, a size and the like of a generating line of each of the projections 131 may substantially, variously vary depending on requirements and treatment environments. Additionally, each of the projections 131 may have a relatively dull and rounded vertex, as well as each of the projections 131 may have a sharp vertex.

The projections 131 may be densely formed on the entire surface of the leading edge portion 130. In this instance, the projections 131 may be arranged in a row along a length of the leading edge portion 130, or may be arranged in a spiral shape of a predetermined pitch along an outer circumference of the leading edge portion 130. Alternatively, the projections 131 may be arranged irregularly so that a gap between neighboring projections may be minimized. In addition, the arrangement of the projections 131 may be substantially, variously changed.

Figure 4:
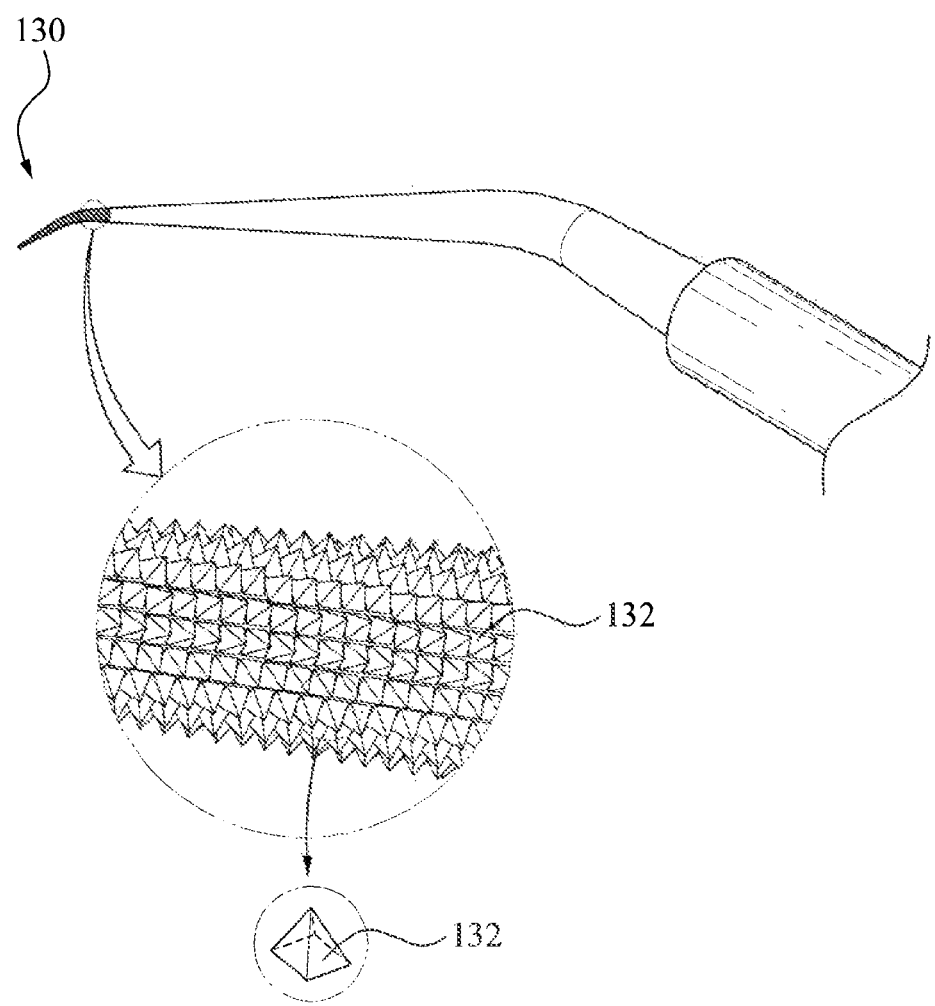
Figure 5:
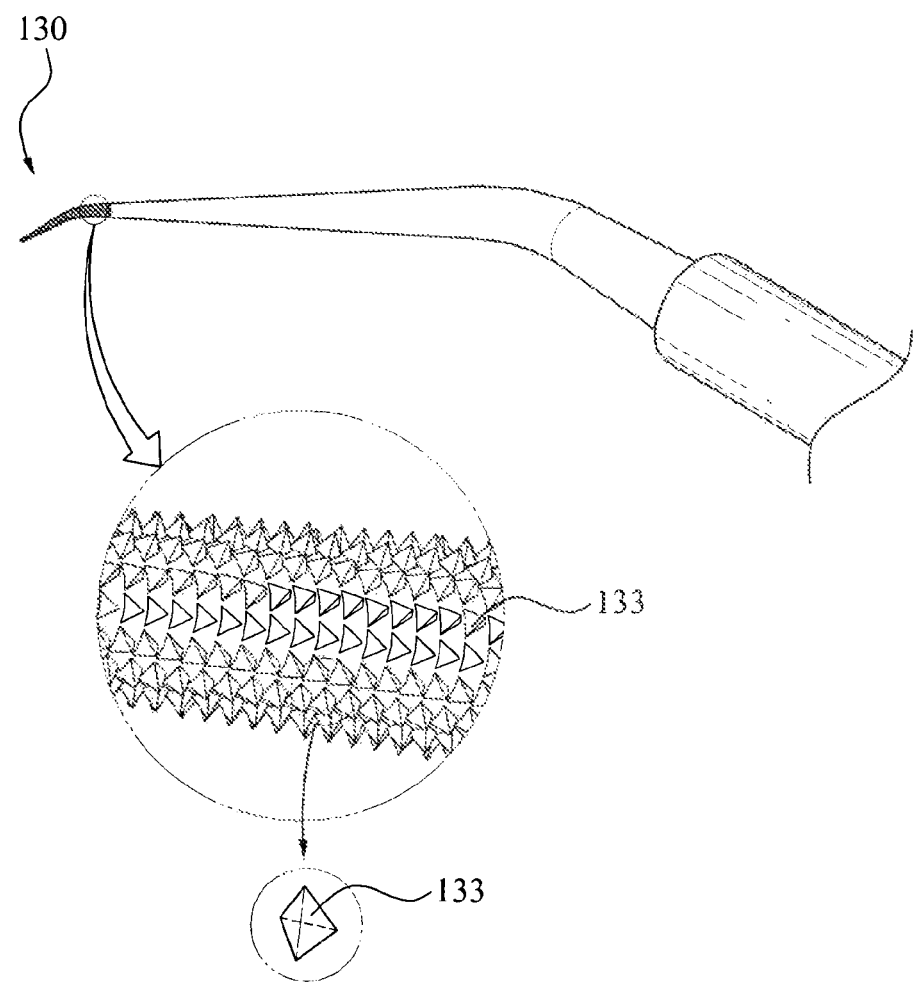

According to another embodiment of the present invention, each of projections may have a polygonal pyramid shape. For example, as shown in FIG. 4, each of projections 132 may have a quadrangular pyramid shape having a sharp vertex and a quadrangular base side. As shown in FIG. 5, each of projections 133 may have a triangular pyramid shape having a sharp vertex and a triangular base side. In this instance, each of the projections 132 and 133 may have a vertical quadrangular pyramid shape, or a vertical triangular pyramid shape in which an axis is perpendicular to a base side, or may be inclined at a predetermined angle with respect to the surface of the leading edge portion 130. Additionally, a size, a shape, arrangement of a projection and the like may be substantially, variously changed.

Figure 6:
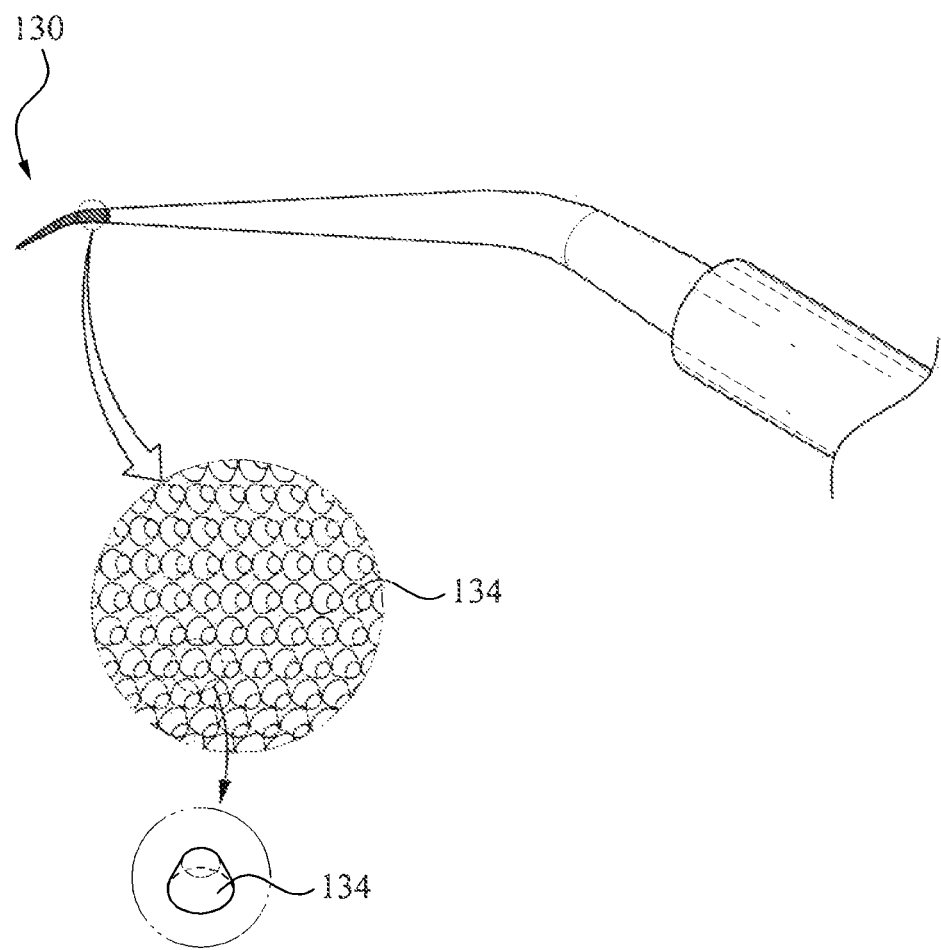

According to still another embodiment of the present invention, each of projections 134 may have a frustum shape having a circular or polygonal contact surface as a cutting edge. For example, as shown in FIG. 6, projections 134 may each have an oblique cylindrical shape in which a base side and an upper side (hereinafter, a side that faces the base side and that is in contact with a target is referred to as an 'upper side') have different diameters. Additionally, the projections may have a hemispherical or ellipsoidal solid shape that has a circular or elliptical base side.

For reference, the frustum may include a truncated cone (an oblique cylinder) that is a frustum of a general circular cone, a truncated quadrangular pyramid (an oblique parallelepiped) that is a frustum of a general quadrangular pyramid, and a truncated triangular pyramid (an oblique parallel pentahedron) that is a frustum of a general triangular pyramid, and may also include a polyhedron, such as a hexahedron, a pentahedron, and the like. A shape and a structure of the frustum may variously vary depending on requirements and design specifications. Therefore, the present invention is not limited thereto or restricted thereby.

In the above embodiments, an example in which projections having the same shape are formed have been described, however, a plurality of projections having different shapes or different sizes may be formed.

Figure 7:
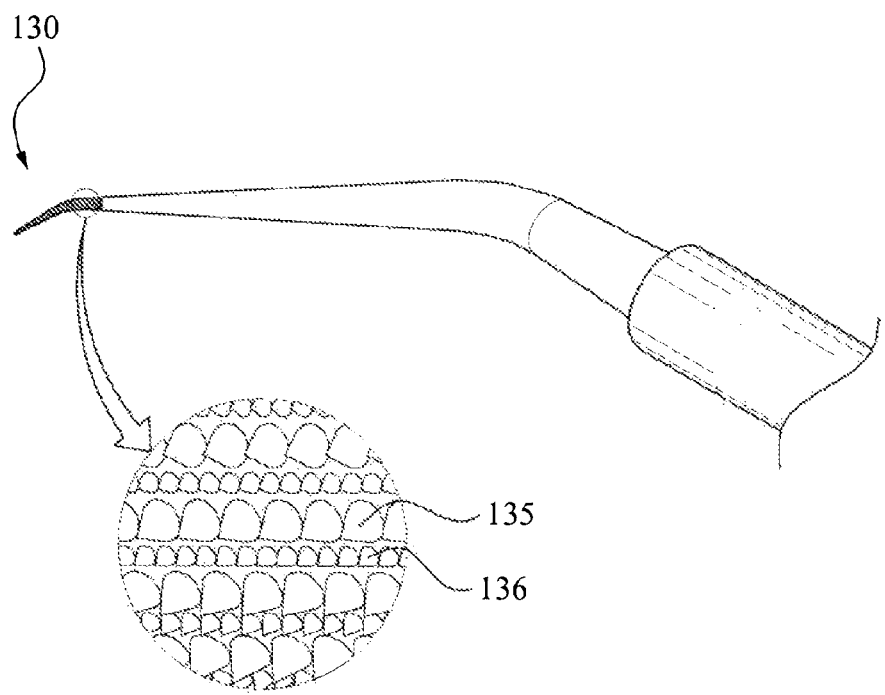

For example, protrusions each having a different size may be formed. A plurality of main protrusions having a predetermined size and shape may be arranged at regular intervals, and a plurality of auxiliary protrusions that are smaller than the main protrusions may be arranged between the main protrusions. For example, as shown in FIG. 7, main protrusions 135 having a circular conic shape may be arranged in a row along a length of the body portion 120, and auxiliary protrusions 136 may be arranged in a row between columns of the main protrusions 135. In this instance, the main protrusions 135 and the auxiliary protrusions 136 may have similar shapes with different sizes. For example, the main protrusions 135 and the auxiliary protrusions 136 may each have one of a circular conic shape, a polygonal pyramid shape (for example, a quadrangular pyramid shape, a triangular pyramid shape, and the like), a frustum of the circular conic shape and the polygonal pyramid shape (for example, a truncated conic shape, a truncated polygonal pyramid shape, and the like), a circular cylindrical shape, a polyhedral shape (for example, a pentahedral shape, a hexahedral shape, and the like), and an ellipsoidal shape.

Unlike the embodiment of FIG. 7, the main protrusions 135 and the auxiliary protrusions 136 may have different shapes.

Additionally, the main protrusions 135 and the auxiliary protrusions 136 may be arranged alternately for each column, or a plurality of columns of the main protrusions 135 and a plurality of columns of the auxiliary protrusions 136 may be arranged alternately. In this instance, a number of columns in which the main protrusions 135 and the auxiliary protrusions 136 may be substantially, variously changed.

According to an embodiment, the main protrusions 135 and the auxiliary protrusions 136 having different sizes (or shapes) may be arranged in a row along the length of the leading edge portion 130, or may be arranged in a spiral shape of a predetermined pitch along the outer circumference of the leading edge portion 130. In this instance, the main protrusions 135 and the auxiliary protrusions 136 having different sizes may each form a screw thread and a threaded rod.

Figure 8:
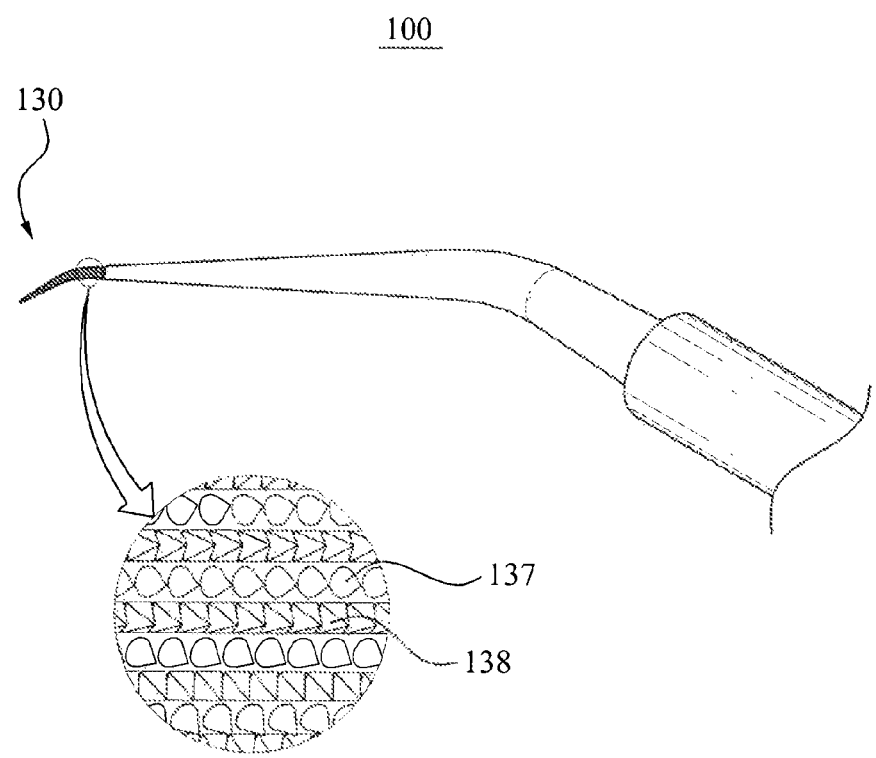

According to another embodiment, a plurality of projections having different shapes may be formed. For example, as shown in FIG. 8, main protrusions 137 and auxiliary protrusions 138 each having a predetermined shape may be provided, and may have different shapes and different sizes. In an example, each of the main protrusions 137 may have a shape of a vertical circular cone in which an axis is perpendicular to a base side, and each of the auxiliary protrusions 138 may have a shape of a vertical quadrangular pyramid in which an axis is perpendicular to a base side.

However, the present invention is not limited by the drawings, and the main protrusions 137 and the auxiliary protrusions 138 may each have one of a circular conic shape, a polygonal pyramid shape (for example, a quadrangular pyramid shape, a triangular pyramid shape, and the like), a frustum of the circular conic shape and the polygonal pyramid shape (for example, a truncated conic shape, a truncated polygonal pyramid shape, and the like), a circular cylindrical shape, a polyhedral shape (for example, a pentahedral shape, a hexahedral shape, and the like), and an ellipsoidal shape. Additionally, the main protrusions 137 and the auxiliary protrusions 138 may have similar shapes, or different shapes. Similarly, the main protrusions 137 and the auxiliary protrusions 138 of FIG. 8 may be arranged in a row along the length of the leading edge portion 130, or may be arranged in a spiral shape of a predetermined pitch along the outer circumference.

Alternatively, since the cross-sectional area of the leading edge portion 130 tapers towards the end, the projections may become smaller towards the end of the leading edge portion 130.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The invention claimed is:

1. A method for manufacturing an ultrasonic tip for an apicoectomy, the method comprising:
    forming a feedstock by mixing a metal powder including stainless steel with a binder;
    injecting the feedstock to form an injection-molded part having a plurality of projections integrally formed on the surface thereof;
    performing debinding to remove the binder from the injection-molded part;
    sintering the injection-molded part; and
    performing annealing to increase a ductility and facilitate a bending of the sintered part,
    wherein the ultrasonic tip comprises a shank portion, a body portion, and a leading edge portion, and wherein the projections include one or more projections selected from the group consisting of projections having a circular conic shape, a polygonal pyramid shape, a truncated conic shape, a truncated polygonal pyramid shape, a circular cylindrical shape, a polyhedral shape, and an ellipsoidal shape, and
    wherein the projections are arranged linearly along a length of the leading edge portion, and not spirally along a circumference of the leading edge portion.

2. The method of claim 1, wherein the annealing is performed at a temperature of 400° C. to 1250° C. so that the body portion and the leading edge portion are bendable.

3. The method of claim 2, further comprising:
    bending a part of the leading edge portion, wherein the bending is performed after the annealing.

4. The method of claim 2, wherein each of the projections has the same size and the same shape.

5. The method of claim 2, wherein the projections have different sizes and different shapes.

6. The method of claim 2, wherein the projections include one or more projections having a circular or elliptical base side.

7. The method of claim 2, wherein the leading edge portion has a cross-sectional area that tapers towards an end of the leading edge portion, wherein the projections become smaller towards the end.

8. A method for manufacturing an ultrasonic tip for an apicoectomy, the method comprising:
    forming a feedstock by mixing a metal powder including stainless steel with a binder;
    injecting the feedstock to form an injection-molded part having a plurality of projections integrally formed on the surface thereof;
    performing debinding to remove the binder from the injection-molded part;
    sintering the injection-molded part; and
    performing annealing to increase a ductility and facilitate a bending of the sintered part,
    wherein the ultrasonic tip comprises a shank portion, a body portion, and a leading edge portion, and wherein the projections include one or more projections selected from the group consisting of projections having a circular conic shape, a polygonal pyramid shape, a truncated conic shape, a truncated polygonal pyramid shape, a circular cylindrical shape, a polyhedral shape, and an ellipsoidal shape,
    wherein the leading edge portion has a cross-sectional area that tapers towards an end of the leading edge portion, and wherein the projections become smaller towards the end.

9. The method of claim 8, wherein the annealing is performed at a temperature of 400° C. to 1250° C. so that the body portion and the leading edge portion are bendable.

10. The method of claim 9, further comprising:
    bending a part of the leading edge portion, wherein the bending is performed after the annealing.

11. The method of claim 9, wherein each of the projections has the same size and the same shape.

12. The method of claim 9, wherein the projections have different sizes and different shapes.

13. The method of claim 9, wherein the projections are arranged linearly along a length of the leading edge portion, or are arranged spirally along a circumference of the leading edge portion.

14. The method of claim 13, wherein the projections are arranged linearly along a length of the leading edge portion.

15. The method of claim 9, wherein the projections include one or more projections having a circular or elliptical base side.

\* \* \* \* \*